United States Patent
Ebstein

(10) Patent No.: US 9,750,958 B2
(45) Date of Patent: Sep. 5, 2017

(54) DOSIMETRIC SCINTILLATING SCREEN DETECTOR FOR CHARGED PARTICLE RADIOTHERAPY QUALITY ASSURANCE

(71) Applicant: Steven M. Ebstein, Newton, MA (US)

(72) Inventor: Steven M. Ebstein, Newton, MA (US)

( * ) Notice: Subject to any disclaimer, the term of this patent is extended or adjusted under 35 U.S.C. 154(b) by 286 days.

(21) Appl. No.: 14/528,079

(22) Filed: Oct. 30, 2014

(65) Prior Publication Data
US 2015/0071408 A1    Mar. 12, 2015

Related U.S. Application Data

(63) Continuation-in-part of application No. 13/775,325, filed on Feb. 25, 2013.

(60) Provisional application No. 61/602,301, filed on Feb. 23, 2012, provisional application No. 61/897,532, filed on Oct. 30, 2013.

(51) Int. Cl.
*G01J 1/00* (2006.01)
*A61N 5/10* (2006.01)

(52) U.S. Cl.
CPC .... *A61N 5/1075* (2013.01); *A61N 2005/1076* (2013.01)

(58) Field of Classification Search
CPC .... G01T 1/17; G01T 7/00; G01T 1/02; G01T 1/161; G01T 1/29
See application file for complete search history.

(56) References Cited

U.S. PATENT DOCUMENTS

| | | | | |
|---|---|---|---|---|
| 4,081,673 A * | 3/1978 | Swindell | ........ | A61B 6/025 250/237 R |
| 5,493,121 A * | 2/1996 | Fitzpatrick | ........ | G01T 1/20 250/361 R |
| 6,285,740 B1 * | 9/2001 | Seely | ........ | H05G 1/30 250/367 |
| 7,412,024 B1 * | 8/2008 | Yun | ........ | A61B 6/484 250/367 |

(Continued)

OTHER PUBLICATIONS

Kandarakis et al. "Experimental and theoretical assessment of the performance of Gd2O2S:Tb and La2O2S:Tb phosphors and Gd2O2S:Tb-La2O2S:Tb mixtures for X-ray imaging" Euro. Radiol. (2001) p. 1083-1091.*

(Continued)

*Primary Examiner* — David Porta
*Assistant Examiner* — Mamadou Faye
(74) *Attorney, Agent, or Firm* — Pandiscio & Pandiscio

(57) ABSTRACT

An apparatus and method are provided for performing Quality Assurance of complex beams of penetrating radiation inside a patient. A detector with a transverse scintillating screen images the radiation inside a tissue phantom with high spatial resolution. The scintillator is comprised of a mixture of two or more scintillators emitting different spectra of light and having different characteristic responses as a function of the beam LET value. The optics relaying the scintillation output have variable transmission with wavelength, further shaping the spectrum of light transmitted to the imaging sensor which also has spectrally varying sensitivity. Parameters of the scintillator construction, the optics, and the imaging sensor are chosen so the output of the composite detector is proportional to a characteristic of the input beam, for example the dose deposited as a function of depth inside the tissue phantom.

19 Claims, 11 Drawing Sheets

(56) References Cited

U.S. PATENT DOCUMENTS

| | | | |
|---|---|---|---|
| 7,515,681 B2 | 4/2009 | Ebstein | |
| 8,080,801 B2* | 12/2011 | Safai | G01T 1/202 250/368 |
| 2011/0248188 A1 | 10/2011 | Brusasco et al. | |
| 2012/0205530 A1 | 8/2012 | Beaulieu et al. | |

OTHER PUBLICATIONS

Boon, S. N., Dosimetry and Quality Control of Scanning Proton Beams, 1998.

Koba, Y. et al., Scintillation Efficiency of Inorganic Scintillators for Intermediate-Energy Charged Particles, Progress in Nuclear Science and Technology; 2011, vol. 1, p. 218-221.

Murray, R. B. et al., Scintillation Response of Activated Inorganic Crystals to Various Charged Particles, Physical Review, 1961, vol. 122, No. 3, p. 815-826.

Safai, S. et al., Development of an inorganic scintillating mixture for proton beam verification dosimetry, Physics in Medicine and Biology, 2004, vol. 49, p. 4637-4655.

Schippers, J. M. et al., Applications in radiation therapy of a scintillating screen viewed by a CCD camera, Nuclear Instruments and Methods in Physics Research, 2002, A 477, p. 480-485.

* cited by examiner

DOSIMETRIC SCINTILLATING SCREEN DETECTOR FOR CHARGED PARTICLE RADIOTHERAPY QUALITY ASSURANCE

REFERENCE TO PENDING PRIOR PATENT APPLICATIONS

This patent application:

(i) is a continuation-in-part of pending prior U.S. patent application Ser. No. 13/775,325, filed Feb. 25, 2013 by Steven M. Ebstein for DOSIMETRIC SCINTILLATING SCREEN DETECTOR FOR CHARGED PARTICLE RADIOTHERAPY QA, which patent application claims benefit of prior U.S. Provisional Patent Application Ser. No. 61/602,301, filed Feb. 23, 2012 by Steven M. Ebstein for DOSIMETRIC SCINTILLATING SCREEN DETECTOR FOR CHARGED PARTICLE RADIOTHERAPY QA; and (ii) claims benefit of prior U.S. Provisional Patent Application Ser. No. 61/897,532, filed Oct. 30, 2013 by Steven M. Ebstein for DOSIMETRIC SCINTILLATING SCREEN DETECTOR FOR CHARGED PARTICLE RADIOTHERAPY QUALITY ASSURANCE.

FEDERALLY SPONSORED RESEARCH

This invention was made with U.S. Government support under Grant 5R44CA103610-03 awarded by the National Cancer Institute. The U.S. Government has certain rights in the invention.

The three (3) above-identified patent applications are hereby incorporated herein by reference.

FIELD OF THE INVENTION

The present invention pertains to a device and a method for monitoring the spatial characteristics of a beam of penetrating radiation and, more particularly, to quality assurance in particle therapy, namely, ensuring that the dose delivered matches the intended treatment plan.

BACKGROUND OF THE INVENTION

The goal of radiotherapy is to irradiate unhealthy, usually cancerous, tissue or tumors with the aim of killing that tissue while sparing, to the extent possible, the surrounding healthy tissue. This requires that the patient be irradiated with one or more radiation beams that are carefully positioned and shaped in order to precisely deliver the intended quantity of radiation to a specific target volume. In dimensions transverse to the nominal direction of the beam, this shaping is often performed with metal apertures or multi-leaf collimators that define the profile of the beam. The beams are often directed from different angles at the patient, thereby increasing the radiation dose in the intersecting regions. A treatment plan is generated for each irradiation session of a patient that describes the various beam angles, shapes, energies, and quantity of radiation delivered along with the associated maps showing the radiation dose intended for the patient.

With high-energy X-ray beams, the technique of spatially shaping the radiation dose with multi-leaf collimators and multiple beams directed from multiple angles is known as Intensity Modulated Radiation Therapy or IMRT.

Charged particles, typically protons but also heavier ions, are also used for delivering spatially complex radiotherapy treatments. The particle accelerators typically produce a narrow, or pencil, beam that can be focused, collimated, or deflected with magnetic optics, although sometimes the beam is broadened in size or angle by scattering the pencil beam. With particle beams, the shaping can also be effected along the beam direction by varying the energy distribution of the charged particles, as the penetration distance and dose distribution along the particles' tracks depends on their energy. For a monoenergetic ion beam in a homogeneous medium, the absorbed dose versus depth describes a curve known as a pristine Bragg peak as seen at 12 in FIG. 1.

From entrance into the body until close to the penetration depth, the delivered dose, which is proportional to the average linear energy transfer (LET) given in keV/μm due to ionization by the beam, rises slowly along the plateau of the curve. Near the final depth, the LET increases rapidly to a peak, then falls to zero rapidly at the end of the track of the ensemble of particles in the beam, thereby increasing the radiation dose in a narrow volume. The LET value is typically a characteristic of a beam as a function of depth. It is related to the energy loss per unit length dE/dx per unit density, typically given in MeV cm$^2$/g, of each charged particle. dE/dx is a function of the particle energy.

In this specification, the term beam generally refers to a penetrating radiation beam. However, it may either refer to a radiation beam produced by an accelerator, a narrow pencil beam at the output of the beam delivery system, a set of pencil beams delivered within a short time, i.e., a composite beam, or a broad beam restricted by a metal aperture or collimator. A treatment field generally refers to a composite or broad beam with a set of particle energies and a defined spatial distribution delivered within a short time. If either the energies or spatial distribution or both are changed, that generally refers to a new treatment field.

By irradiating with beams having different energies, or by modulating the beam energy as it is applied, the dose distribution can be shaped to deposit maximal dose in an extended volume containing the tumor while delivering reduced dose to the surrounding healthy tissue. An example, shown at 14 in FIG. 1, uses a beam with a set of different energies and fluences arranged to produce a depth-dose curve with a flat maximum, denoted as a spread-out Bragg peak or SOBP. The energy of particles in the beam can be reduced by inserting absorbing elements, typically plastic, upstream of the patient. The energy reduction depends on the thickness of the absorber, so a set or range of energies can be produced with a spatially varying thickness to the absorber or by rotating a wheel with multiple thickness steps and temporally modulating the beam energy.

FIG. 1 highlights one of the differences between radiotherapy using x-rays or charged particles. For an equivalent dose at the depth in the middle of the SOBP, the x-ray beam deposits more dose in front of that depth and after the tail of the Bragg peak, represented by the area between the x-ray dose curve 10 and the charged particle SOBP dose curve 14. This ability to limit the dose to healthy tissue outside of a tumor is a major motivation for delivering radiotherapy with charged particles.

Charged particle beams can also be scanned across the patient if the beam is small enough and scanning magnets are provided to steer the beam in angles away from the central axis of the system. This technique is generally termed pencil beam scanning or PBS. PBS treatments can be delivered without metal apertures or collimators if the scanning magnets can sufficiently define the transverse shape of the composite beam. Typically, more than one radiation field will be applied from a single direction with different energies or energy spectra used for the different fields, thereby shaping the delivered dose at different depths.

Several different forms of PBS are used to deliver radiotherapy. A technique known as Intensity Modulated Proton Therapy or IMPT allows the beam intensity to vary as a function of lateral position by modulating the beam current or modulating the scanning rate. In some scenarios, the beam position is continually scanned and in others it is translated to a series of fixed positions where the beam is turned on for a period of time, a technique called spot scanning. For this approach, the magnetic scanning of the beam defines the shape of the irradiated volume transverse to the beam direction. An approach, which is termed either wobbling or uniform scanning, has the beam scan a given area, typically a regular region like a circle or rectangle, and deliver a uniform dose over that area. A fixed aperture or multi-leaf collimator is positioned between the beam source and the patient to restrict the transverse distribution of radiation.

In all of these various forms of radiotherapy, the standard for positioning and shaping the beam relative to the patient is typically less than one millimeter across a field of regard that can range up to 40 cm in diameter. This requires that the radiation pattern be delivered with precise shaping and positioning of the beam(s) over those scales, as well as in precise amounts so the dose absorbed by the patient matches the prescription of the treatment plan. This requires careful calibration and measurement of the delivery system and the treatment plan, i.e., the beam(s) which will be delivered to the patient, a process referred to as quality assurance or QA. QA measurements are routinely performed that reassure the practitioners that the correct radiation dose will be delivered in the correct amount over the correct spatial distribution to the patient. These measurements are performed with a variety of different radiation detectors.

With the complex series of radiation fields that are used in radiotherapy, especially in charged particle therapy, it is critical to make measurements which predict the absorbed dose inside of a patient, not merely in a plane just outside of the patient. One way this is accomplished is by placing absorbing material, a tissue phantom, in between the beam source and the detector so the radiation incident on the detector corresponds to the radiation incident on the corresponding location(s) inside of the patient. The absorbing material is typically water (since the body is mostly made up of water), sheets of plastic with water-equivalent absorbance, or more complex phantoms with multiple materials.

There exist several different detectors used for performing QA of these radiotherapy beams. Film has been used since the beginnings of radiotherapy to view the beam as delivered to the patient. Various other technologies have been used, including scintillating screen based portal imagers, flat panel devices consisting of a sheet of scintillating crystals atop an array of semiconductor detectors, ionization chambers as single devices, stacked along the beam direction, or arrayed transverse to the beam direction, multi-wire proportional chambers, gaseous electron multiplier (GEM) detectors, and other detectors, etc. Typically, these detectors are one part of the overall system and procedure for performing QA.

Requirements for these detectors include stability, robustness, linearity, accuracy, and precision, i.e., signal to noise ratio (SNR), spatial resolution, and dosimetric accuracy. The detector output should be translatable into a measure of the effective dose delivered to the patient. In addition, marketability factors such as the cost and usability of the detector output are important for the usefulness of a detector for QA applications.

An ideal QA detector would measure the delivered dose inside a tissue phantom with sufficient spatial resolution to validate the treatment plan. In practice, current detectors fall short in one or more respects. Some of the detectors employed, like film and detectors using thin scintillating screens or sheets of crystal, have spatial resolution that exceeds the requirement for beam positioning and shaping. However, their detection signal is not linear with the fluence or LET of the radiation beam, which is required in order to predict the corresponding dose to the patient.

The light output of some scintillators will saturate when a clinically useful fluence is incident. Inorganic scintillators or phosphors such as P11 (ZnS:Ag), P20 (Zn,CdS:Ag), P43 ($Gd_2O_2S$:Tb), P46 ($Y_3Al_5O_{12}$:Ce), and P47 ($Y_2SiO_5$:Ce) have responses that are typically linear with fluence. However, scintillator light output is generally not linear with the LET of the incident particles. A plot of the light output versus depth has the same general shape as the Bragg peak. However, the ratio of the peak value to the value at a point on the plateau differs from the ratio of LET values calculated using accurate physical models or that is measured by a standard detector such as an ion chamber. When the ratio of light output is less than the ratio of LET or absorbed dose, this is termed quenching. The physical explanation is that an abundance of excited atoms provide alternate pathways for excited species to relax by means other than photon emission.

Scintillating screens are used, in conjunction with radiation therapy, for absorbed dose measurement (as described, for example, by J. M. Schippers, S. N. Boon and P. van Luijk, "Applications in Radiation therapy of a scintillating screen viewed by a CCD camera," Nucl Instr. and Meth. A 477, pp. 480-85 (2002), and S. N. Boon, thesis, "Dosimetry and quality control of scanning proton beams" (1998), available online at http://www.ub.rug.nl/eldoc/dis/science/s.n.boon/, and references therein, all of which are incorporated herein by reference). They are also useful for monitoring beam delivery in real time (S. M. Ebstein, High Resolution Proton Beam Monitor, U.S. Pat. No. 7,515,681). However, as those references show, knowledge of the particle beam energy spectrum and careful calibration of the detector response is required to make accurate dosimetric measurements.

Other detectors such as ion chambers are quite linear in their measurement of the fluence and LET, so they are quite accurate in predicting absorbed dose. However, due to their size and complexity, they cannot be made into arrays that can measure the incident radiation distribution with the required resolution.

Due to the limitations of these detectors, a complex system is required to perform and evaluate the QA measurements. Typically, a series of representative measurements are made with detectors that have high spatial resolution but poor dosimetric accuracy or detectors with limited spatial resolution but good dosimetric accuracy. The response of the detectors to the delivered radiation beams is calculated from a model of the beam delivery and detection system and compared to the actual measurements. This approach is described in C. Brusasco and B. Marchand, Device And Method For Particle Therapy Monitoring And Verification, U.S. Patent Application Pub. No. US 201110248188 A1.

However, this approach cannot give complete confidence that the delivered beam matches the plan due to reduced dimensionality of the measurements. In addition, the work required to construct the models and perform the calculations of the expected measurements adds to the cost and complexity of performing QA.

There exists a need for improved detectors, especially for charged particle therapy QA. The beam delivery systems are complex instruments and are required to produce a series of beams with complex shapes and different energy spectra. Current detectors and systems cannot directly measure the delivered dose as a function of depth with sufficient accuracy and spatial resolution to quickly and easily perform the QA task. A detector which combines the high spatial resolution of either film or a scintillating screen detector and the dosimetric accuracy of an ion chamber would be very useful in performing QA of complex radiotherapy treatment plans, especially for IMPT.

SUMMARY OF THE INVENTION

In accordance with preferred embodiments of the present invention, an apparatus and method are provided for performing QA of complex beams of penetrating radiation that produce a spatially varying dose distribution inside of a patient. The apparatus provides for inserting tissue phantom material in between the beam source and a detector. The detector incorporates a scintillator disposed transverse to the nominal direction of the beam and one or more high resolution imaging sensors in optical communication with the scintillator for generating an image of the beam distribution across the scintillator. The scintillator is comprised of a mixture of two or more scintillators emitting different spectra of light and having different characteristic responses as a function of the beam LET value. The means of optical communication of the scintillation output, i.e., the optics, have variable transmission with wavelength, further shaping the spectrum of light transmitted to the imaging sensor. The imaging sensor has sensitivity that varies across the spectrum of light input. Parameters of the scintillator construction, the optics, and the number and types of imaging sensors are chosen so the output of the composite detector is proportional to a characteristic of the input beam. In one embodiment, the characteristic is the dose deposited as a function of depth inside the tissue phantom. In another embodiment, the scintillator is disposed in a thin, planar screen that is oriented perpendicular to the central beam axis. In another embodiment, the scintillator output is communicated to multiple sensors whose outputs are combined numerically to produce an output proportional to the desired characteristic.

In one preferred form of the present invention, there is provided an apparatus for determining the spatial distribution and intensity of penetrating radiation beams characterized generally by a propagation direction inside a body, the apparatus comprising:

a tissue phantom disposed between the radiation source and a radiation detector;

a scintillating screen disposed behind the tissue phantom for emitting light in response to the radiation comprising a mixture of at least two scintillators wherein each scintillator has a different characteristic response and a different spectral output;

a means of optical communication of the scintillator output to at least one imaging sensor wherein the means of optical communication has a nonuniform spectral transmission; and at least one imaging sensor in optical communication with the scintillating screen for providing a high resolution imaging sensor output indicative of the spatial distribution and intensity of the radiation beam wherein the imaging sensor has a nonuniform spectral sensitivity;

wherein the composition of the scintillator, the means of optical communication, and imaging sensors are selected so as to comprise a system wherein the imaging sensor output is proportional to a characteristic of the radiation beam incident on the scintillator at each measurement position accessible with the tissue phantom.

In another preferred form of the present invention, there is provided a method for determining the spatial distribution and intensity of penetrating radiation beams characterized generally by a propagation direction inside a body, the method comprising:

providing a tissue phantom between the radiation source and a radiation detector;

providing a scintillating screen behind the tissue phantom for emitting light in response to the radiation comprising a mixture of at least two scintillators wherein each scintillator has a different characteristic response and a different spectral output;

providing a means of optical communication of the scintillator output to at least one imaging sensor wherein the means of optical communication has a nonuniform spectral transmission; and providing at least one imaging sensor in optical communication with the scintillating screen for providing a high resolution imaging sensor output indicative of the spatial distribution and intensity of the radiation beam wherein the imaging sensor has a nonuniform spectral sensitivity;

wherein the composition of the scintillator, the means of optical communication, and imaging sensor are selected so as to comprise a system wherein the imaging sensor output is proportional to a characteristic of the radiation beam incident on the scintillator at each measurement position accessible with the tissue phantom.

In another preferred form of the present invention, there is provided a method for determining the spatial distribution and intensity of penetrating radiation beams characterized generally by a propagation direction inside a body, the method comprising:

providing a tissue phantom between the radiation source and a radiation detector;

providing a scintillating screen behind the tissue phantom for emitting light in response to the radiation comprising a mixture of at least two scintillators wherein each scintillator has a different characteristic response and a different spectral output;

providing a means of optical communication of the scintillator output to an imaging sensor wherein the means of optical communication has a nonuniform spectral transmission; and providing an imaging sensor in optical communication with the scintillating screen for providing a high resolution imaging sensor output indicative of the spatial distribution and intensity of the radiation beam wherein the imaging sensor has a nonuniform spectral sensitivity;

wherein a first composition of the scintillator, a first means of optical communication, and a first imaging sensor are selected so as to comprise a first system wherein the imaging sensor output is proportional to a characteristic of the radiation beam incident on the scintillator at each measurement position accessible with the tissue phantom; and performing characteristic measurements with a penetrating radiation beam and the first system;

wherein one or more of (a) the composition of the scintillator, (b) the means of optical communication, or (c) the imaging sensor is adjusted so as to comprise a second system wherein the imaging sensor output is proportional to a characteristic of the radiation beam incident on the scintillator at each measurement position accessible with the tissue phantom with greater accuracy than with the first system.

BRIEF DESCRIPTION OF THE DRAWINGS

The foregoing features of the invention will be more readily understood by reference to the following detailed description, taken with reference to the accompanying drawings, in which.

DETAILED DESCRIPTION OF THE PREFERRED EMBODIMENTS

In accordance with preferred embodiments of the present invention, the spatial distribution of a beam of penetrating radiation is imaged with a scintillator. The term "penetrating radiation," as used herein, and in any appended claims, refers both to particles with mass, such as protons, as well as to photons, i.e., to electromagnetic radiation such as x-rays or gamma rays. Moreover, in the case of massive particles, the particles are typically charged, such as protons or heavier atomic ions, however, neutrons or other electrically neutral particles may also be detected, and their beams imaged within the scope of the present invention.

Figure 1:
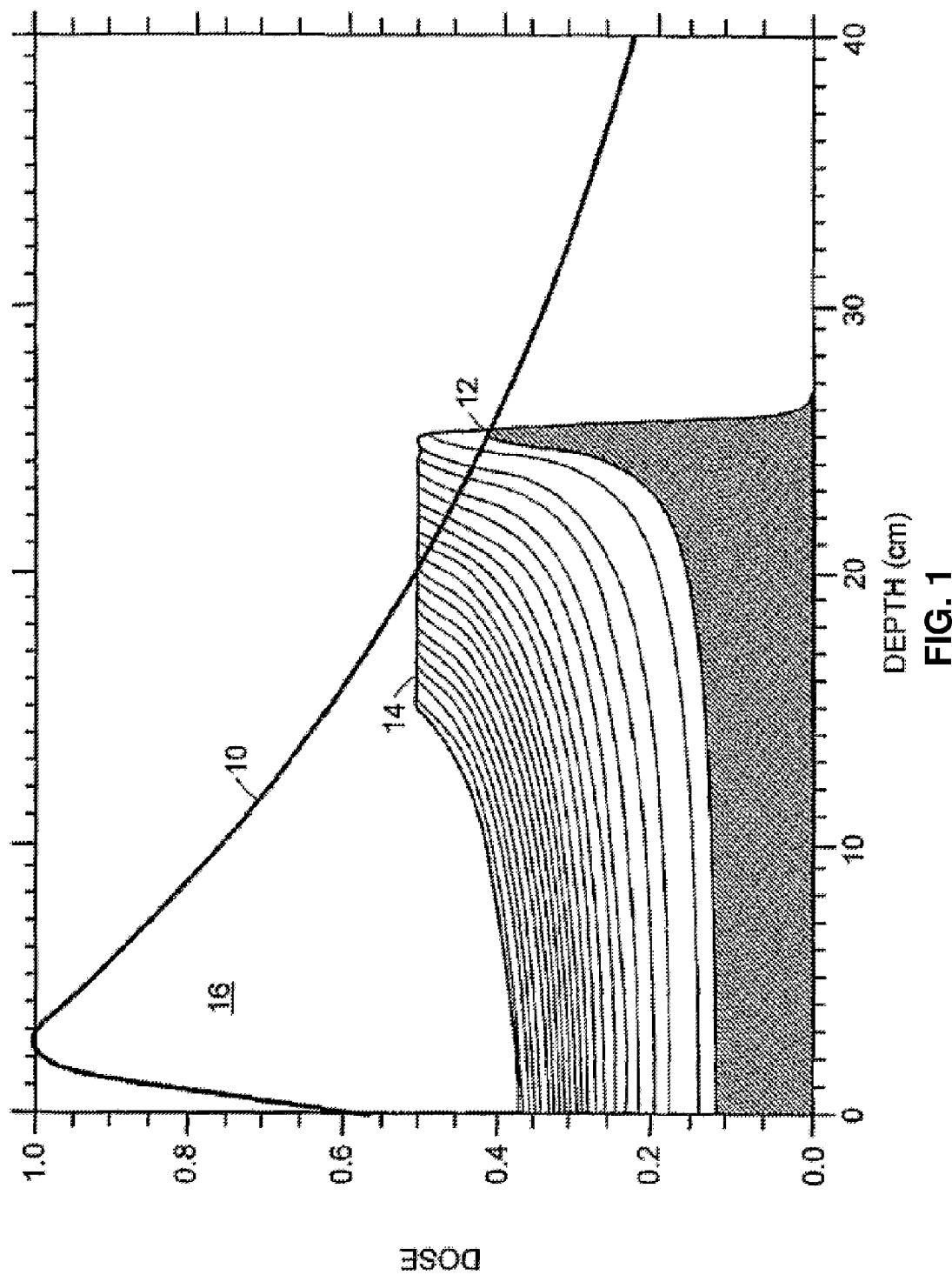
FIG. 1 depicts the relative radiation dose from a photon beam, a pristine proton beam (Bragg peak), and a spread out Bragg peak (SOBP) using protons composed of multiple pristine proton Bragg peaks of different energies. The area between the curves is the excess dose from a photon beam.
Figure 2:
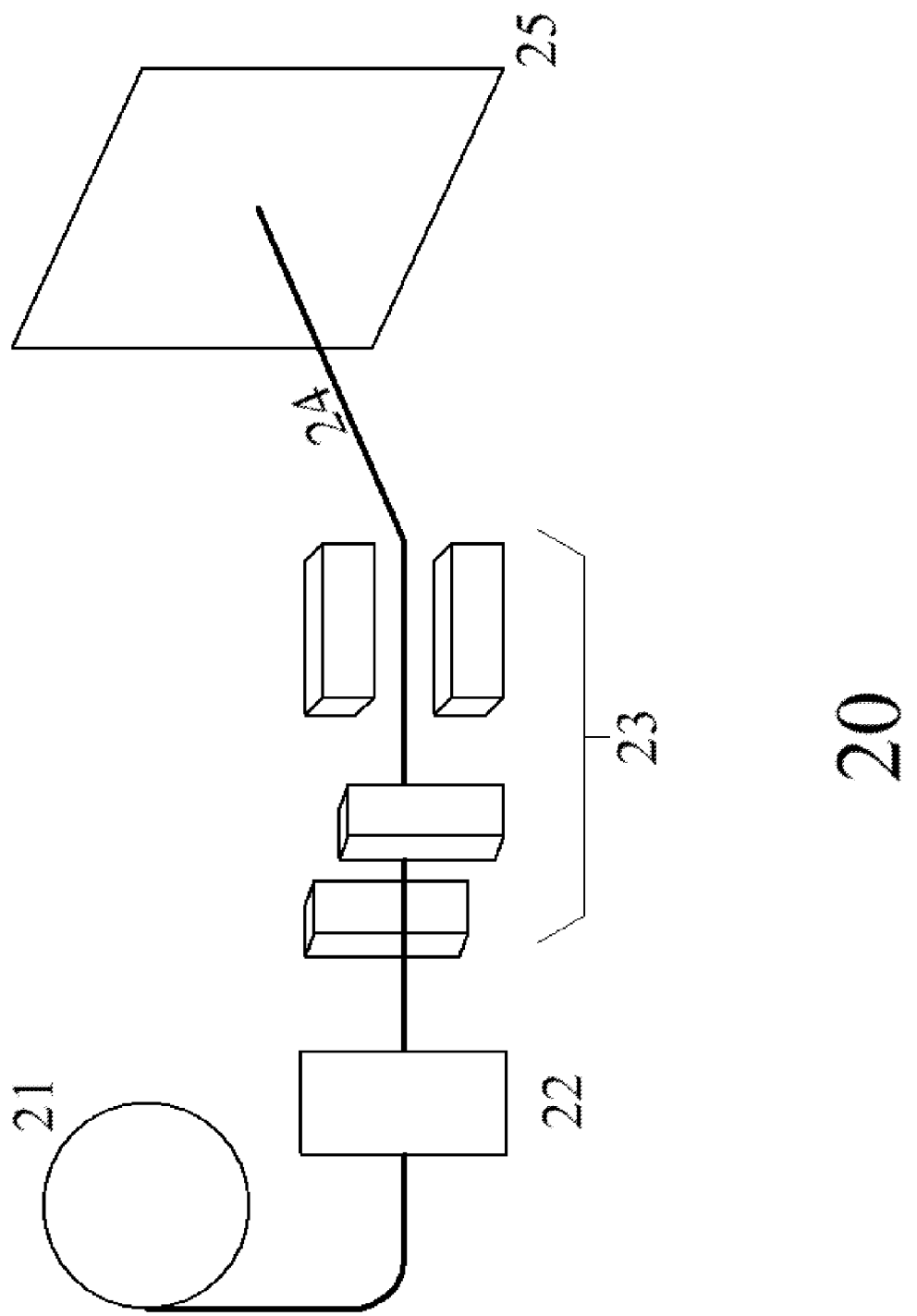
FIG. 2 shows a schematic depiction of a system for delivering a spatially complex radiation beam.

Referring to FIG. 2, a system for delivering a spatially complex radiation beam is designated generally by 20. The system consists of a radiation source, 21, and a means of setting the energy of the radiation, 22, setting the fluence, and means for shaping the transverse spatial distribution of the radiation, 23. In the case of charged particle beams, the shaping means can comprise a scatterer which scatters a unidirectional beam into a beam with a wide angular spread in combination with a fixed or variable collimator or aperture which defines the shape of the beam. Alternatively, the shaping means can comprise two orthogonal scanning magnets which can steer the angle of a pencil beam, 24, from a virtual point located near the magnets across a field of regard, 25.

Figure 3:
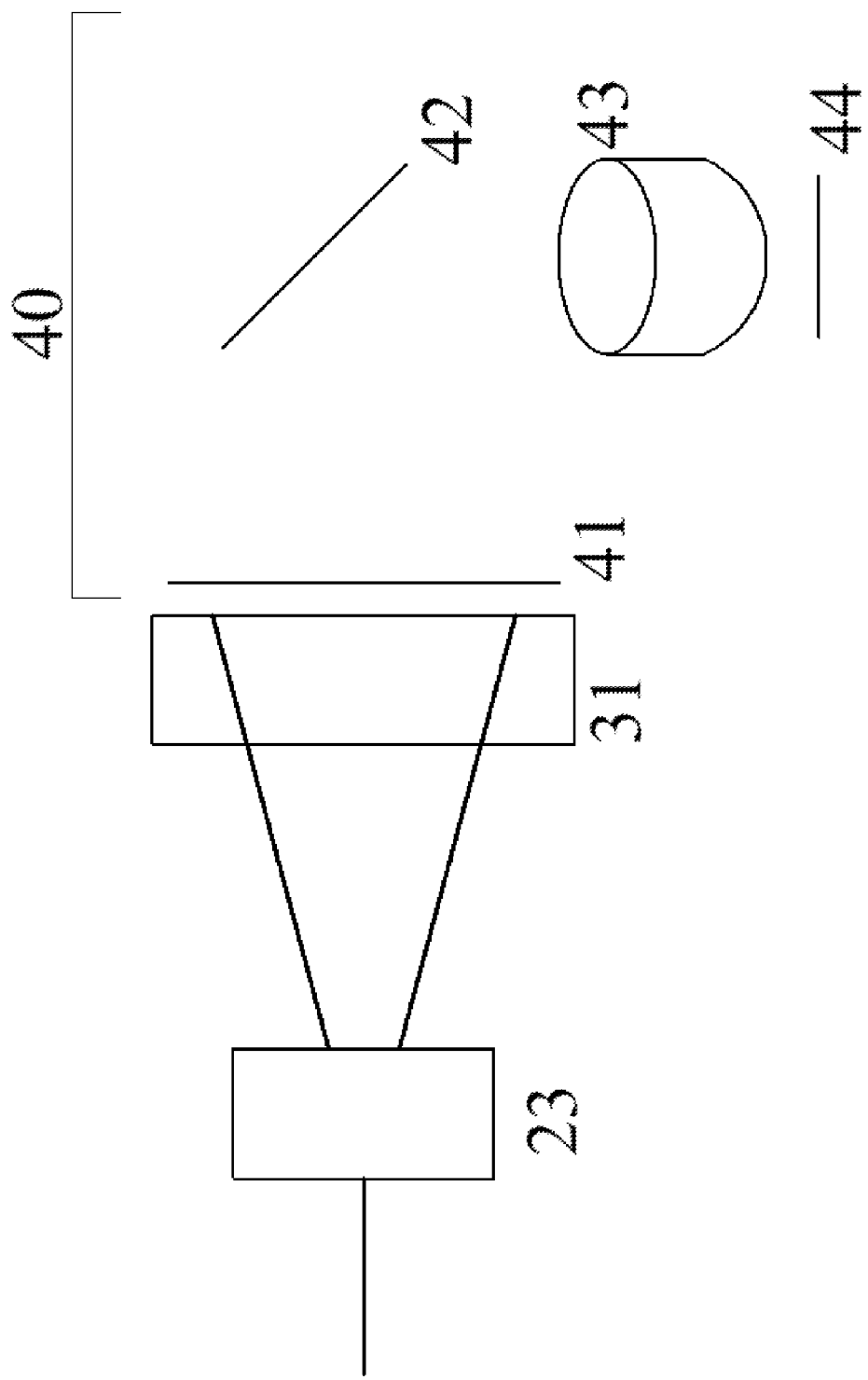
FIG. 3 shows a schematic depiction of the QA apparatus including tissue phantom material, a scintillating screen, and optics relaying the image to an imaging sensor.

Referring to FIG. 3, a QA apparatus consists of a tissue phantom 31 disposed between the beam shaping means and the detector 40 which images the radiation beam. There is provision for varying the effective depth within the phantom, e.g., by varying the thickness of the phantom material, where the detector is located. For example, the tissue phantom may consist of a series of sheets of a polymer material, e.g., a water-equivalent plastic. Sheets may be added or removed so as to vary the effective depth within the phantom where the detector images the beam. In order to simulate measurement at depth within a body, the detector and tissue phantom are typically translated away from the beam source so as to keep the position of the initial surface of the phantom at the same distance from the beam source.

Alternatively, the tissue phantom may comprise a water tank. With the beam directed downwards, as is possible with many radiotherapy delivery systems which comprise a rotating gantry, the water level in the tank can be continually varied. As water is added to the tank, the water tank and detector can be translated downward, away from the beam source, so as to preserve the distance from the beam source to the top of the water layer, thereby simulating measurement at depth within a body. If the water tank comprises a bellows-like apparatus, the thickness of the water layer can be varied with a beam that is not vertical.

The detector comprises a thin scintillating screen 41, denoted the scintillator, at least one imaging sensor 44, and a means of optical communication of the scintillation light from the screen to the sensor, 42 and 43. In order for the detector output to match a characteristic such as the absorbed dose, the scintillator comprises a mixture of two or more scintillating materials comprising a thin layer bound to a supporting substrate, typically a thin plastic film such as Mylar. Since the output of a single material will not typically match the desired characteristic as a function of depth within the tissue phantom, the scintillator composition comprises a mixture of materials whose combined output, in combination with the rest of the apparatus, can match the desired characteristic.

Figure 4:
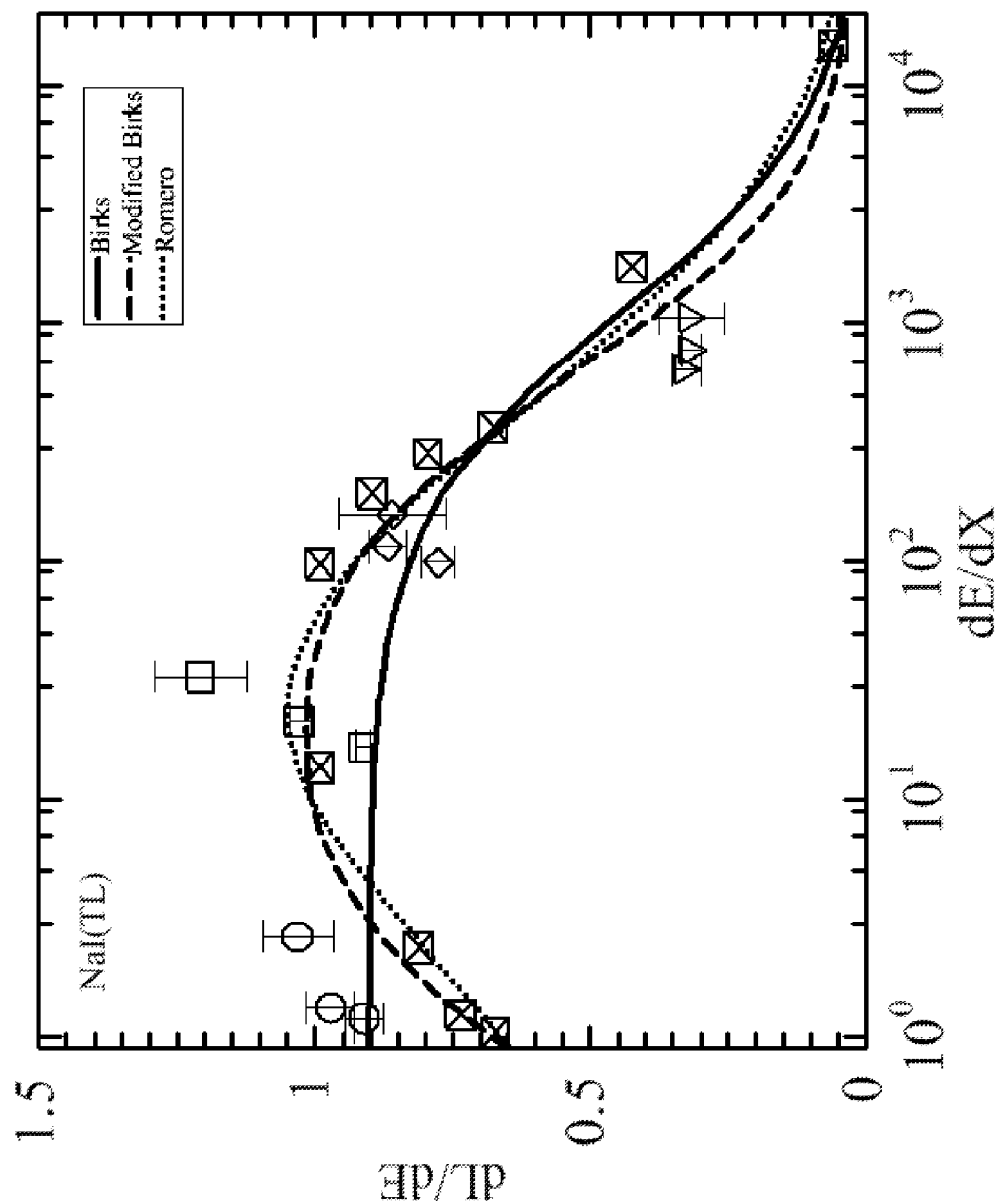
FIG. 4 shows the luminous efficiency of a scintillator versus dE/dx.

For example, it is known that many scintillators such as GSO, LYSO, Y3Al5O12:Ce (P46), Gd2O2S:Tb (P43), and Y2SiO5:Ce (P47) exhibit quenching with increasing dE/dx or LET. That is, their light output per deposited energy, dL/dE, decreases monotonically with increasing dE/dx such as occurs within the Bragg peak. However, there are scintillators such as NaI(Tl), CsI(Tl), ZnS:Ag (P11) and (Zn, Cd)S:Ag (P20) which show anti-quenching behavior, i.e., dL/dE is not monotonic and increases with dE/dx for some values. Examples of both quenching and anti-quenching behavior are shown in R. B. Murray and A. Meyer, Scintillation Response of Activated Inorganic Crystals to Various Charged Particles, Phys. Rev. Vol 122, No. 3, pp. 815-826 (1961), Y. Koba, H. Iwamoto, K. Kiyohara, T. Nagasaki, G. Wakabayashi, Y. Uozumi, N. Matsufuji, "Scintillation Efficiency of Inorganic Scintillators for Intermediate-Energy Charged Particles," Progress in Nuclear Science And Technology, Vol. 1, p. 218-221 (2011), S. Safai, S. Lin, and E. Pedroni, "Development of an inorganic scintillating mixture for proton beam verification dosimetry," Phys Med Biol. 2004 Oct. 7; 49(19):4637-55 and S. Safai, Inorganic Scintillating Mixture And A Sensor Assembly For Charged Particle Dosimetry, U.S. Pat. No. 8,080,801. FIG. 4 shows the luminous efficiency of several scintillators as a function of dE/dx.

One can generate an output signal that is proportional to a desired characteristic by combining the outputs from different scintillators in ways detailed below. It is apparent that for these common scintillators, different characteristic responses such as quenching and anti-quenching behavior may also be accompanied by different spectral outputs. Therefore, the detection and combination of the signals from each scintillator may depend on their varying spectral outputs. In order to generate an output signal that is proportional to a desired characteristic, several parameters must be chosen so that they work in combination to produce a signal that is linear in the desired characteristic. These parameters include (a) the scintillator composition; (b) the spectral transmission of the optics; and (c) the number of and spectral sensitivity of imaging sensors which detect the scintillated light.

In a preferred embodiment of the invention, the scintillating screen comprises a mixture of a quenching and an anti-quenching inorganic scintillator comprising a substrate comprised of a thin sheet of supporting material, e.g., polyester sheet, and a thin layer of the scintillating material ranging from 10-1000 mg/cm$^2$ in thickness. In addition to the scintillating material, a polymer material is typically included as a binding agent to dimensionally stabilize the scintillator mixture and adhere the scintillating layer to the substrate that supports it. The substrate, the scintillator mixture and any binding agents will affect the characteristics of the scintillation light output. The substrate may be clear or partially reflective. The inorganic scintillators are typically opaque and will scatter or absorb some or all of the scintillation light output from the portions of the scintillating layer proximal to the source of the radiation beam. A variety of binding agents are known to the art, including a variety of single component and dual component optical cements and epoxies which cure by heat, UV light, or chemically. These binding agents are selected because of one or more characteristics including their cost, ease of use, their ability to form a uniform scintillating layer, their optical clarity, and their ability to withstand radiation without darkening, yellowing, or otherwise suffering radiation damage.

In a preferred embodiment of the invention, the light from the scintillator is communicated to the imaging sensor by a mirror and a compound lens close to the imaging sensor. The mirror, designated the fold mirror, directs light from the scintillator to the side so the imaging sensor can be located outside of the radiation beam. The lens forms a high resolution image of the scintillating screen on the imaging sensor so there is an accurate, high resolution sampling of the radiation beam as it is incident on the scintillator. Typically, both the fold mirror and the lens will have a nonuniform spectral effect on the scintillation light transmitted to the sensor. The reflectance of the fold mirror, especially when used at a 45 degree angle, varies with wavelength over the range of visible scintillators, and lens transmission varies with wavelength, as well.

In a preferred embodiment of the invention, the imaging sensor comprises a thermoelectrically cooled CCD detector.

Safai et al. have disclosed a mixture scintillator which has one component with a quenching characteristic and one with an anti-quenching characteristic, which in combination produces a signal that has a quenching characteristic different than either component alone. QA of the treatment would be simpler if the signal is proportional to the deposited dose. However, the spectral output of each scintillator component is typically not identical. Thus, using the typical measure of scintillator efficiency, output power per input power (W/W), is not sufficient to predict the detection signal. The signal will depend on the interaction of the spectral content of the scintillator output with the spectral transmission of the optics and the spectral sensitivity of detectors which receive the light from the mixture scintillator. A signal proportional to deposited dose may result with certain optics and detectors but not with others.

The spectral content and quantity of the scintillation light is a function of several multiplicative factors within the linear range of the scintillator and the sensor. First, each scintillating component has a characteristic spectrum $S_n(\lambda)$ as well as an areal density $\rho_n$. Most important, its luminous efficiency $dL/dE=E_n(LET, F)$, i.e., the unit light output is a function of LET and the overall fluence F. The output is attenuated by a factor $A_n(\lambda)$ due to the self-absorption and scattering by the scintillation layer which depends on the scintillator density and the characteristics of the binder such as the binder areal density and transmission. The imaging sensor will typically have a sensitivity $Q(\lambda)$ that reflects the effective quantum efficiency of the sensor, as a function of wavelength, in addition to a gain factor that depends on the electronic amplification and digitization of the photodetection signal. Finally, the spectral transmission $T(\lambda)$ of the optics transmitting the scintillation light to the sensor also determines the detected signal.

Thus, the detection signal D(LET, F) per deposited energy equals $$D(LET, F) = \sum_n \int d\lambda \rho_n S_n(\lambda) E_n(LET, F) A_n(\lambda) Q(\lambda) T(\lambda)$$

For this equation, we have assumed that the characteristics of the scintillating screen are uniform across its area. While that is only true with a given accuracy—scintillating screen thickness can typically vary by several percent across a screen tens of cm in size—the variation is generally independent of LET and multiplies D(LET) uniformly as a function of position or angle which can be calibrated by a flat field correction. In addition, evidence from Boon is that the spectral content of the scintillation output does not vary with LET for some common scintillators.

In order for the detection signal to match a characteristic of the radiation beam, the densities of the components of the mixture must be engineered so that the detection signal matches that characteristic, for a given spectral transmission $T(\lambda)$ and spectral sensitivity $Q(\lambda)$. For a dosimetric detector, the desired characteristic is that the detection output is proportional to the energy deposited, i.e., D(LET, F) is essentially independent of the LET value and the fluence. For a two component scintillator, that can be accomplished if one component shows decreasing output with LET (quenching), the other shows increasing output with LET (anti-quenching), and the proportions of the two components are such that the combination has uniform output with LET. Within a range of densities, the proportions should reduce to a ratio of the density of the two components.

However, it may be difficult to design that ratio in advance. Factors such as $A_n(\lambda)$ factor are not well understood and hard to control, as it can be difficult in practice to precisely control the absolute value of $\rho_n$ deposited on the substrate and its uniformity. Factors such as $Q(\lambda)$ are typically average values for sensors tested with a specific input beam of light. A particular sensor with different conditions of the input beam may yield a measurably different efficiency as a function of wavelength due to interference effects resulting from the thickness of a semiconductor sensor, for example.

Figure 5:
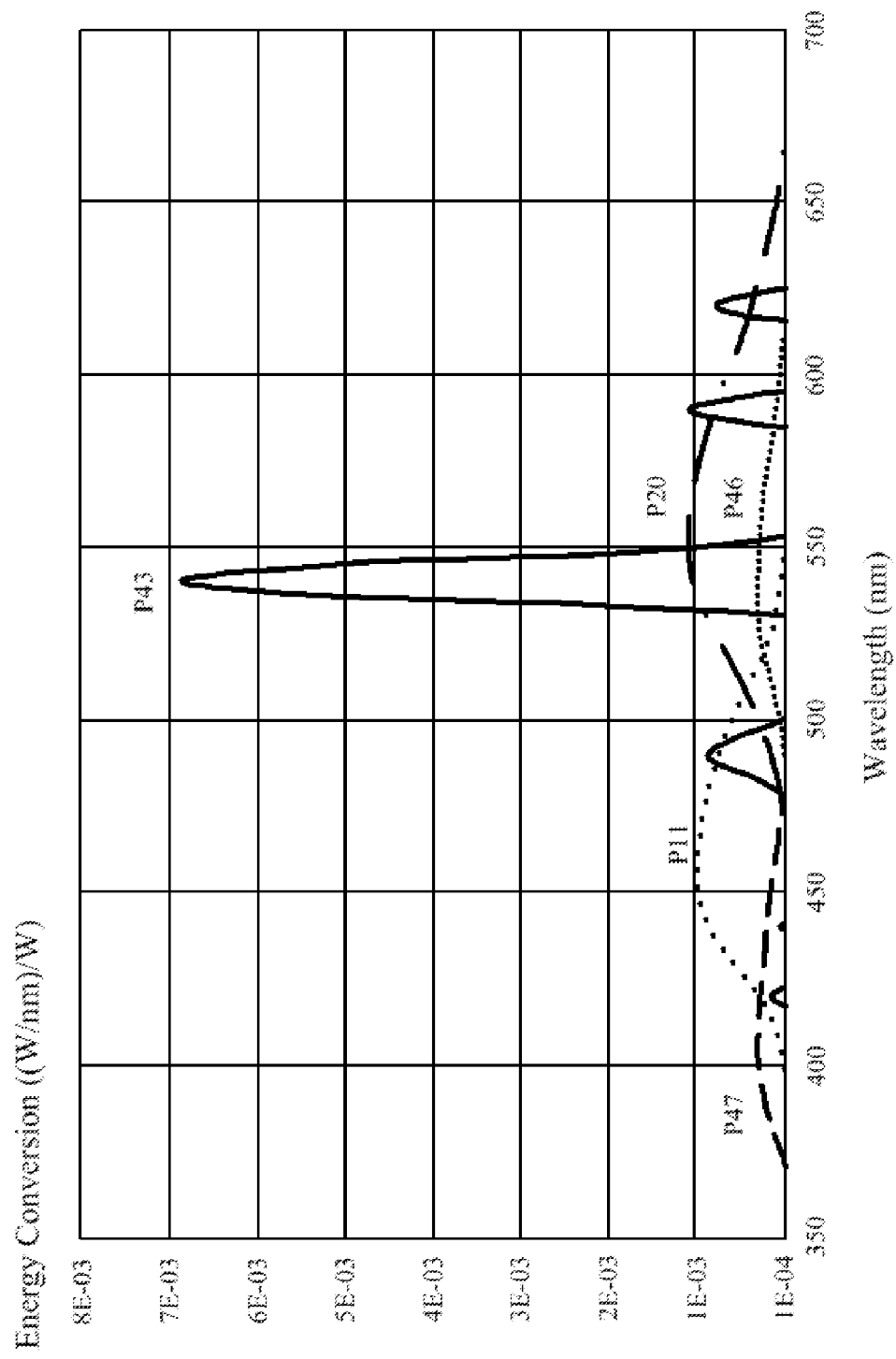
FIG. 5 shows the spectral content of scintillator output for various scintillators.
Figure 6:
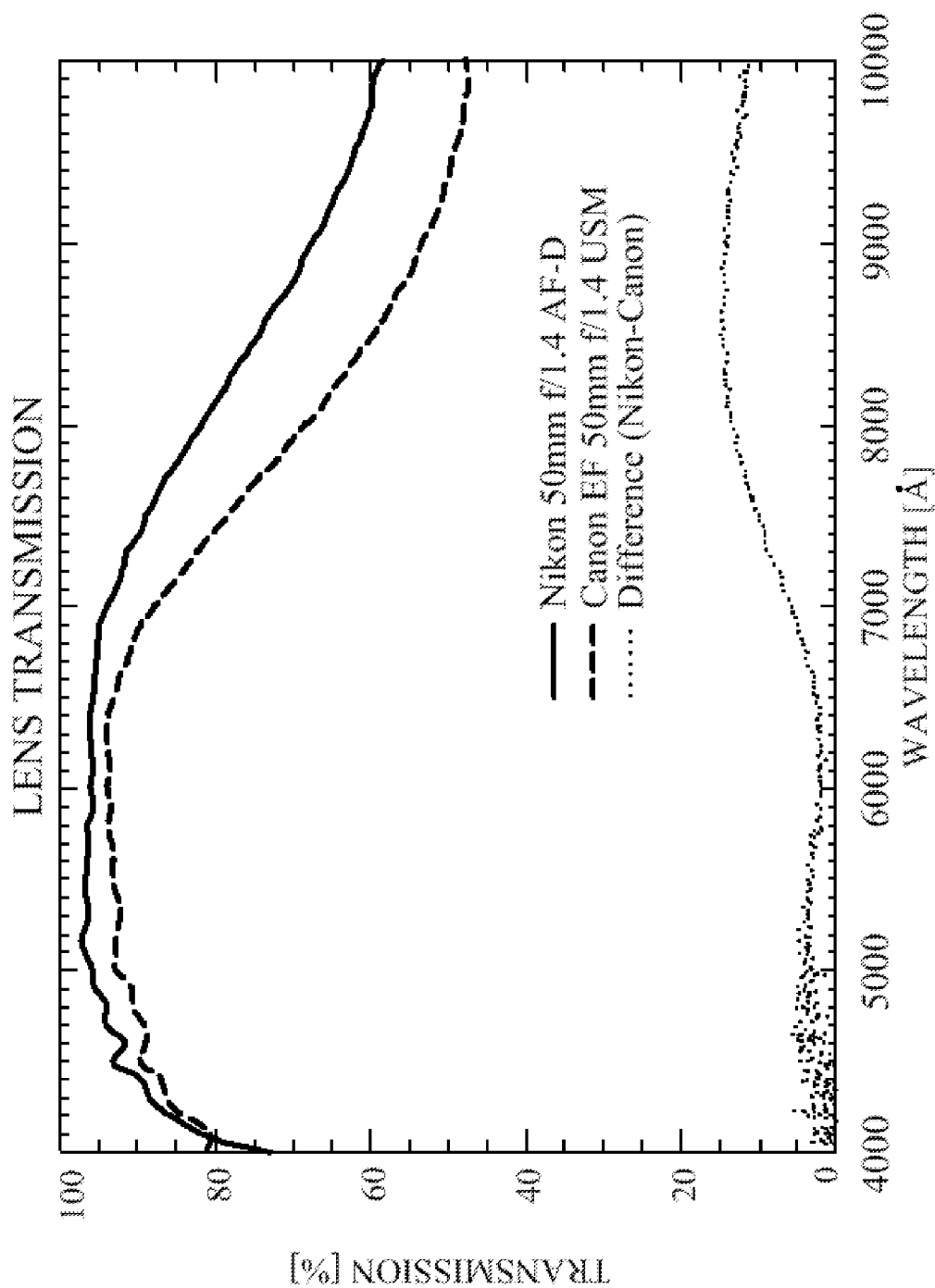
FIG. 6 shows exemplary spectral transmission of compound lenses.

It is possible to tailor the specifications of the optics to compensate for such variations. FIG. 5 shows the considerable variation in the spectral content of the light output of different inorganic scintillators. Thus, the relative contribution of different components of a scintillator mixture to the detection signal can be adjusted by varying the spectral throughput of the optics. The optics transmission function $T(\lambda)$ can be modified by including an element in the optics with variable transmission or reflection as a function of wavelength. In the case of the fold mirror, different reflective coatings such as aluminum, protected aluminum, and various dielectric coatings have non-uniform spectral reflectivity as a function of wavelength. In the case of the lens, different optical glasses have non-uniform spectral transmission. In addition, coatings applied to the glass can have non-uniform spectral transmission. FIG. 6 shows exemplary transmission curves for compound lenses. Furthermore, a color filter can be used with a lens to enhance or diminish various portions of the spectrum.

Figure 7:
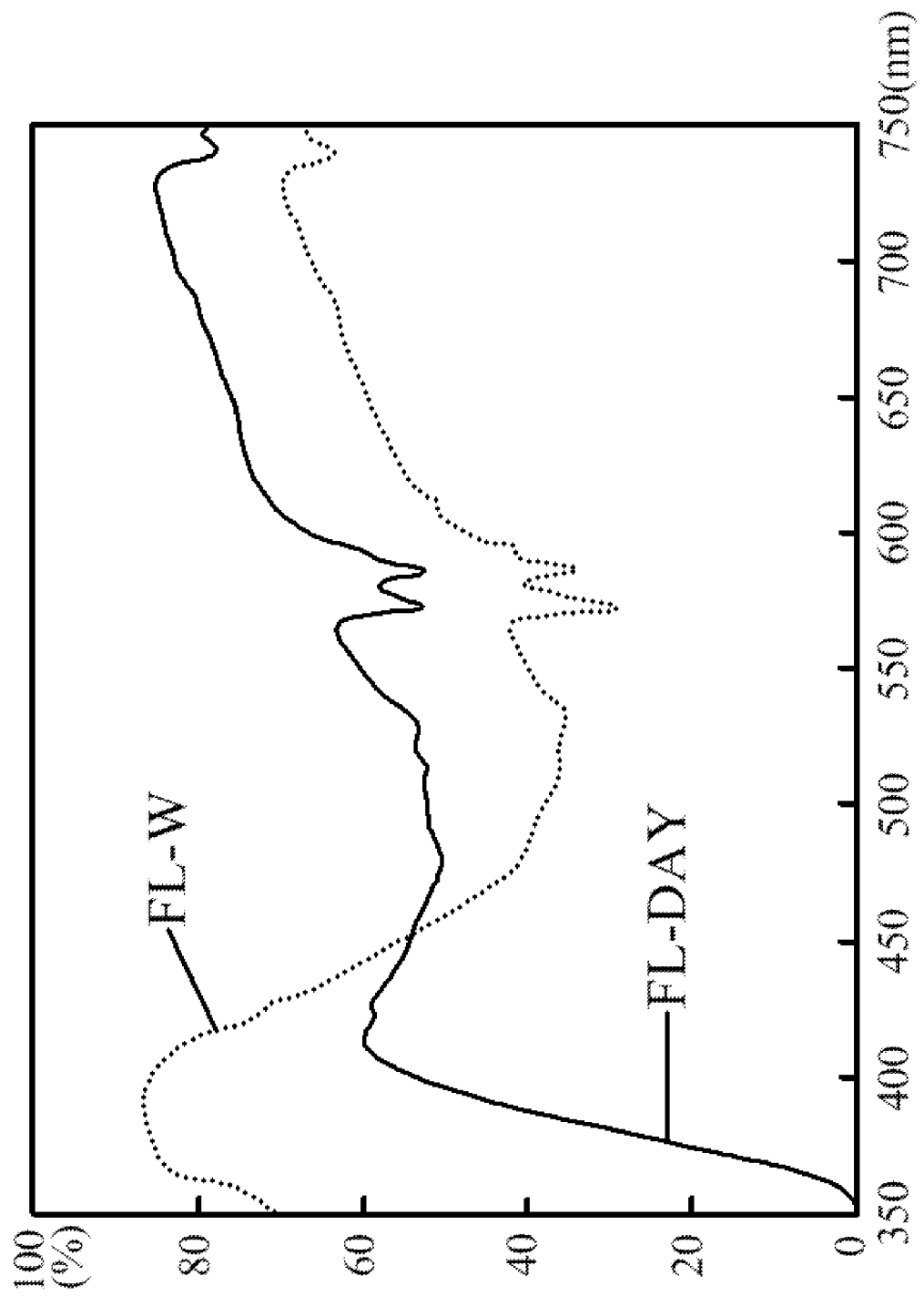
FIG. 7 shows exemplary spectral transmission of colored glass filters.

Colored filters such as Wratten filters, Schott colored glass, and Hoya colored glass can be used for this purpose. FIG. 7 shows exemplary transmission curves for colored glass filters. In addition, numerous filters used for color temperature adjustment, color correction, and light balancing are available. These latter filters are typically designed to correct the effective color (black body) temperature from artificial (tungsten or fluorescent) light to that of sunlight, or vice versa. They often come in a series which can apply smaller or larger color corrections depending on the input lighting or desired output.

It is also possible to employ variable optical components in order to modify the spectral response and hence the degree to which the detection signal matches the desired characteristic. For example, variable optical filters are available with changeable passbands or transmission properties that are modified by changing the temperature of the filter, the voltage across a liquid crystal transmissive element, or by some other means.

Another consideration is that properties of the system components may vary over time due to gradual modification of their properties by aging, slow chemical reactions, or radiation damage. For example, radiation exposure can color or darken optical glasses and optical cements such as the polymer binder in the scintillator, or it can introduce crystal defects into the scintillating material that change the efficiency of the scintillator. The performance of optical coatings can change over time, e.g., if they absorb moisture. Absorbing dyes in colored filters can change, chemically, over time to alter their transmission properties. Any of these changes will affect the elements of the right-hand side of the equation describing the detection signal given above.

Some of these variations in output over time do not affect the basic ability of the system to measure the appropriate characteristic. A spectrally uniform reduction of the overall signal, e.g., due to a colorless (gray) darkening of an optical element, effectively multiplies the detection signal equation by a constant factor independent of the wavelength $\lambda$. This multiplicative or scale factor can be calibrated by measuring the detection response to a radiation beam whose fluence and energy spectrum are known from measurements with other detectors.

Other variations can affect the ability of the system to measure the appropriate characteristic. Variations that change the relative contributions of the various components in the scintillation mixture to the detection signal can change whether the system linearly measures the appropriate characteristic of the radiation or not. Those variations may comprise a differential change in (a) the output of the scintillator components or (b) a change in how that scintillator output is transmitted or detected. For example, one of the optical elements could undergo a colored darkening of a material due to radiation damage which would reduce the contribution from a first scintillator component more than from a second scintillator component.

A variation in one element of the equation can be compensated for by changing one or more of the other elements of the system. For example, the colored darkening from the previous example could be compensated for by adding a filter which reduces transmission from the second component more than from the first component. Alternatively, if radiation damage reduces output from a first component of the scintillator more rapidly than from a second component of the scintillator, a filter could be added that preferentially transmits the spectral output of the first component relative to the second component so as to compensate.

It may be difficult to predict the elements of the right-hand side of the detection equation with sufficient accuracy. As noted, the scintillator output can be quite sensitive to the scintillator mixture, including the binder, and the layer thickness. Moreover, the values of some elements of the equation may have significant uncertainties due to process variation. There may also be practical considerations where technical specifications for some components are unavailable and it may be impractical to measure those specifications of the components. In those cases, some assumptions about the specifications of those elements can be made in order to generate an initial design of the system. The design would include selection of the mixture proportions and the various components.

The initial design can be tested by performing calibration measurements with a well-characterized radiation beam, preferably monoenergetic, and observing the detection signal as a function of depth inside the tissue phantom. Due to the uncertainties, the signal may not match the desired characteristic to a sufficient accuracy. In that case, the design can be modified by changing either the scintillator composition, the optical system, or the imaging sensor. For example, if dose is the desired characteristic and it is found that the detection signal using a two-component scintillator exhibits a quenching characteristic, another scintillator could be fabricated with the fraction of the quenching phosphor reduced relative to the initial design.

Another approach involves adding or changing an optical filter that enhances the contribution of one component of the scintillator. Referring to the previous example, a filter could be added that has higher transmission for the spectral content of the anti-quenching component than for the spectral content of the quenching component. A filter with the necessary transmission ratio for the two components can adjust the output of the system so it matches the desired characteristic response. In the case of dosimetry, the adjusted system would not exhibit quenching or anti-quenching.

The images from the imaging sensor must undergo some processing in order to render the image value at each pixel proportional to the light incident on the sensor. It is known to the art that two point correction consisting of subtraction of a bias value and multiplication of the result by a gain factor is generally required to linearize the output of an imaging detector. Moreover, these two point corrections typically vary across the imaging sensor and from one copy of a sensor to another so these correction factors are typically specific to a particular detector and take on different values for each pixel of the sensor. We thus speak of the bias and gain images or arrays that are used to process the raw sensor output, since the correction factors typically vary for each pixel.

A series of calibrations are employed to measure the two point correction factors, i.e., recording the sensor response when no radiation is incident (a dark exposure) or the response to a uniform radiation pattern (flat field). In some cases, the sensor output is non-linear with the underlying characteristic, e.g., the intensity or fluence of the incident radiation. In these cases, a non-linear transformation of the sensor signal is performed after its response has been carefully calibrated. In what follows, the resulting signals described are those after the imaging sensor output has been processed to produce a signal proportional to the incident light.

Figure 8:
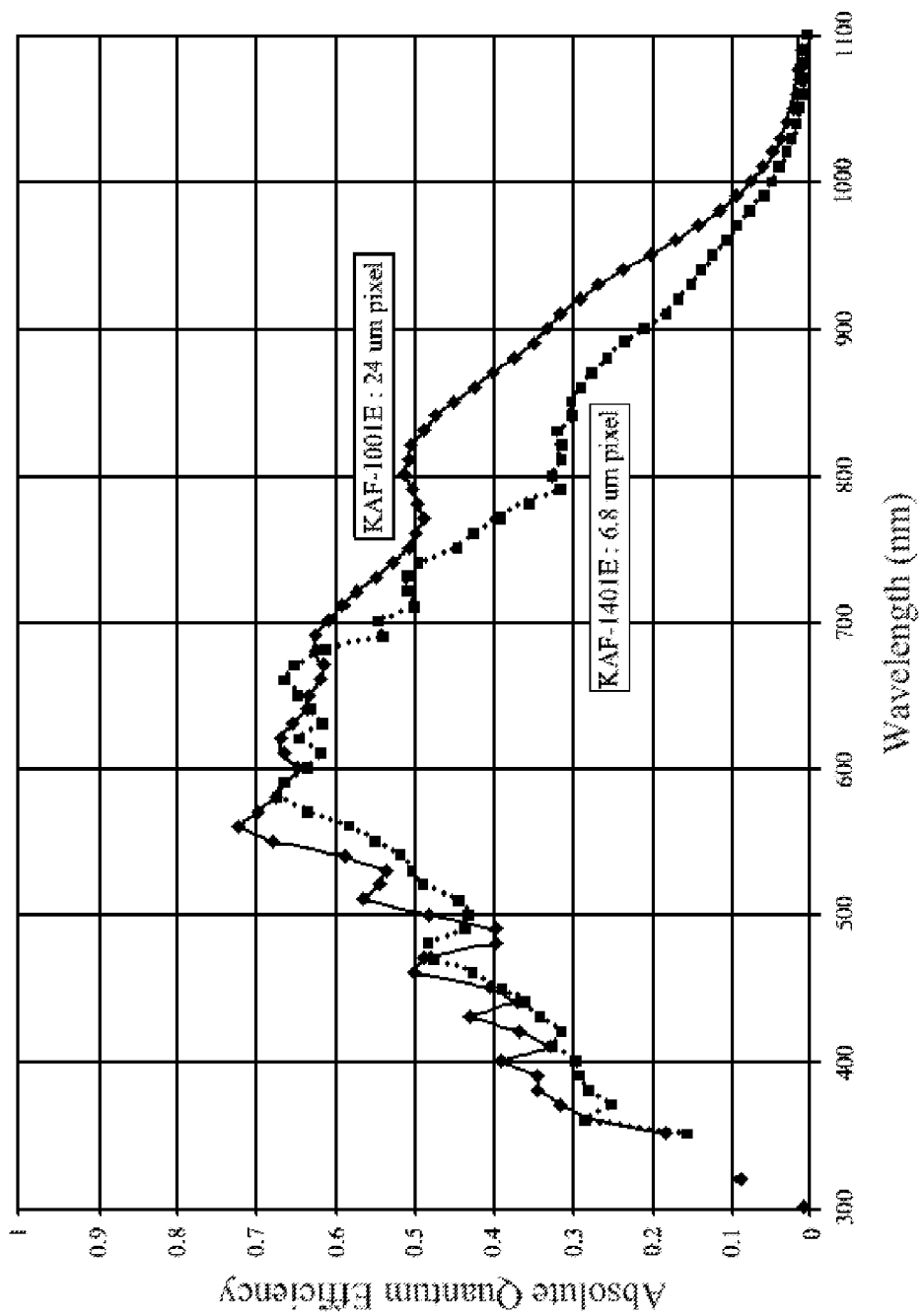
FIG. 8 shows exemplary spectral response of an imaging sensor.

In accordance with a preferred embodiment of the invention, the scintillator comprises a mixture of two components, by weight, of 25% P11 and 75% P43 in a layer with areal density 120 mg/cm$^2$ on a thin polyester sheet with a polymer binder. The resulting screen has transverse dimensions several centimeters or greater in order to simultaneously measure an area with clinical significance, i.e., an area that surrounds a tumor. The optics comprise a 45 degree first surface mirror of enhanced aluminum coated on glass and a Canon EF camera lens with 50 mm focal length. The imaging sensor comprises a Kodak KAF two-phase CCD employing a transparent gate. FIG. 8 shows the typical sensitivity of this CCD as a function of wavelength. With this composition, the image output is proportional to the radiation dose as measured by a Markus ion chamber.

Note that this composition of the scintillator comprises an anti-quenching blue phosphor, P11, and a quenching yellow-green phosphor, P43. This choice of a scintillator mixture with significantly different color outputs enables the detection properties to be easily tuned with spectrally-varying components that enhance blue versus yellow and green or vice versa.

A favorable aspect of this composition is that it does not use toxic materials. Recently, the desire to reduce the use of hazardous materials such as lead in solder has led to regulatory requirements for electronic and other instruments which do not use such materials. This trend is exemplified by designation of ROHS (reduction of hazardous substances) qualified components, which are now required in some jurisdictions. Other scintillators such as P20 or (Zn, Cd)S:Ag include cadmium, a hazardous material.

Figure 9:
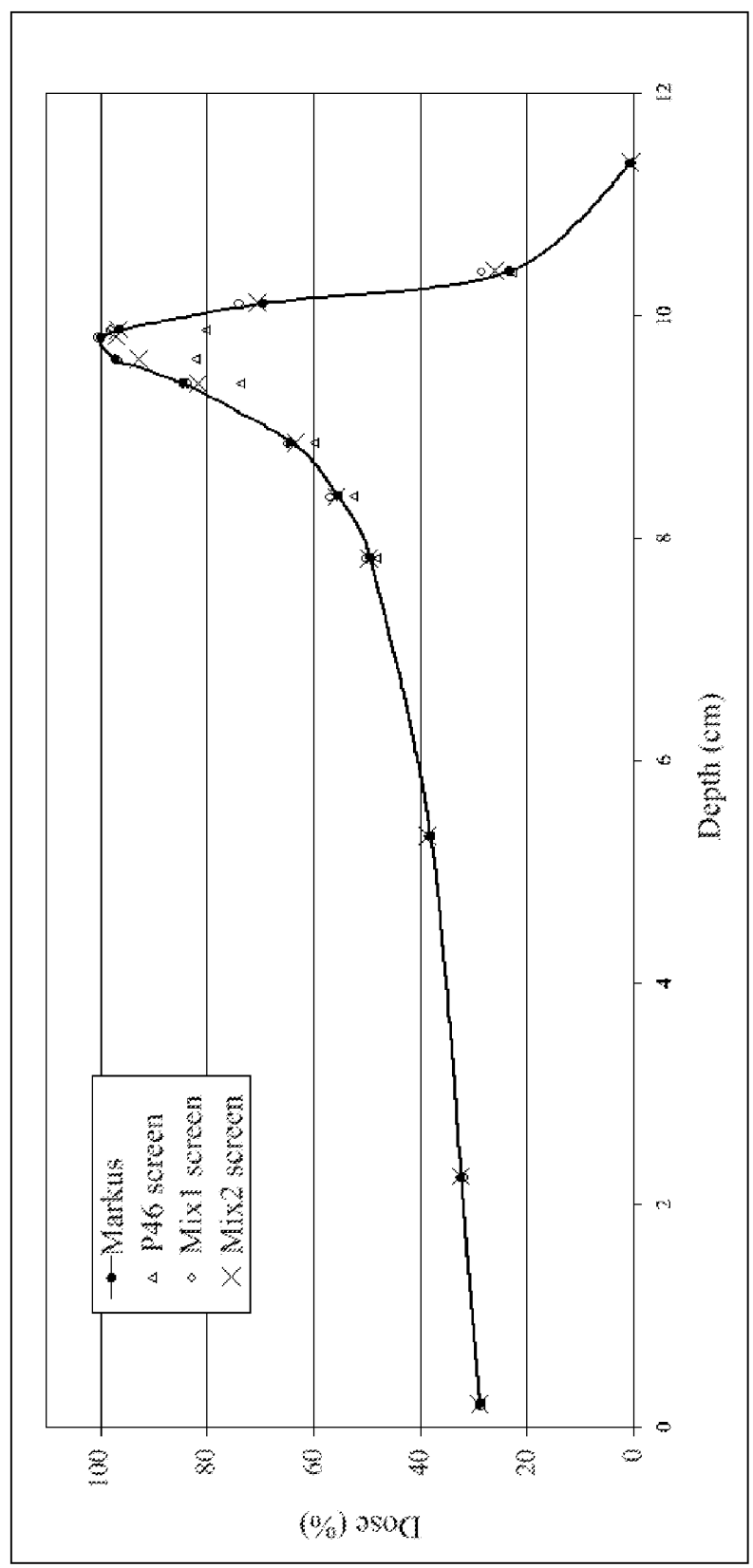
FIG. 9 shows depth dose measurements with a Markus ion chamber and several scintillators.
Figure 10:
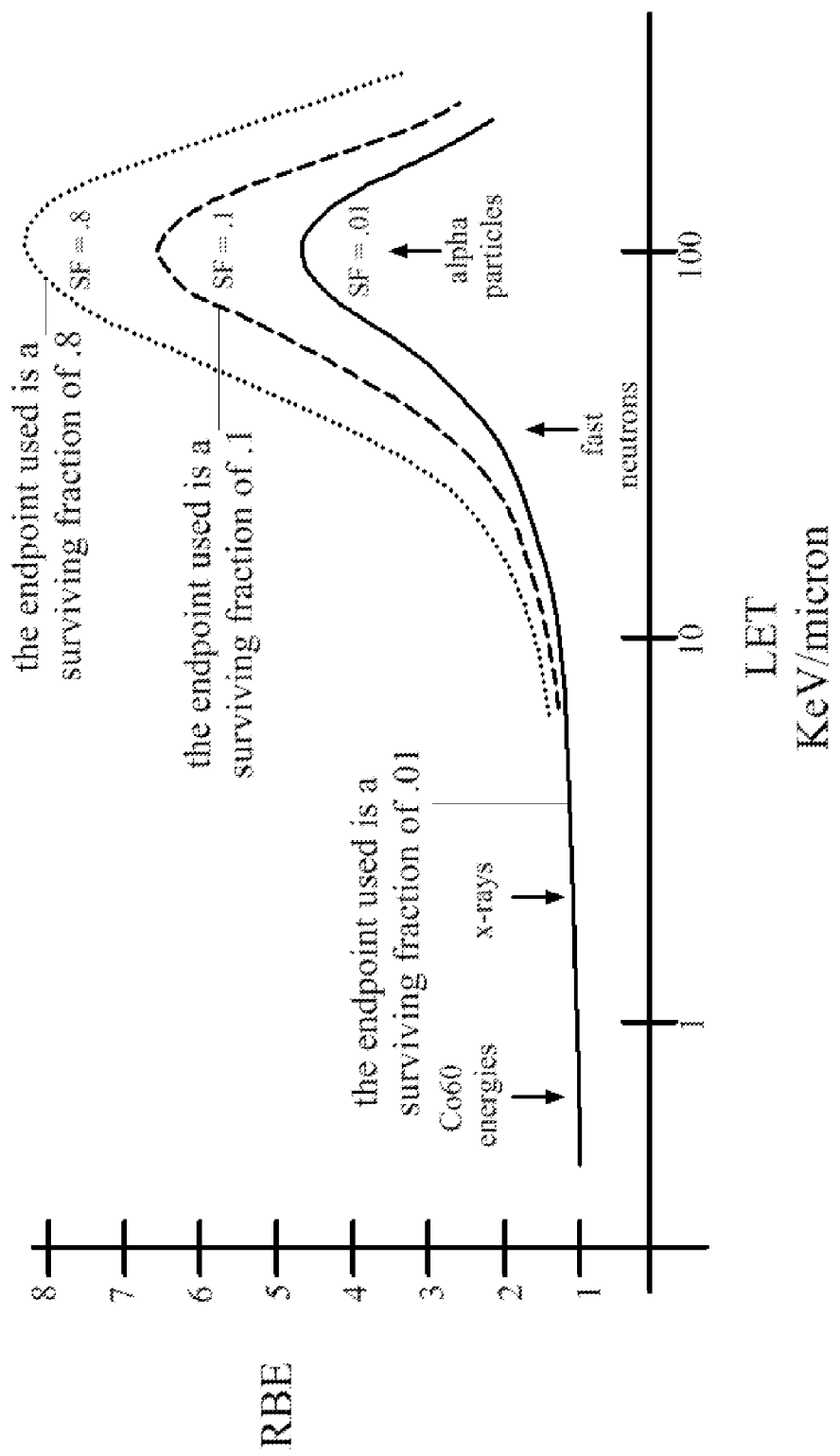
FIG. 10 shows exemplary Relative Biological Effectiveness (RBE) versus Linear Energy Transfer (LET).

FIG. 9 shows the results of measurements with a Markus ion chamber, a quenching scintillator (P46), and two mixture scintillators irradiated by a narrow energy spectrum proton beam with varying thicknesses of a plastic absorber. The "Mix1" scintillator was designed with two scintillator components whose proportions and thickness, together with the optics and imaging sensor, produce an output that matches the dose as measured by the Markus chamber. The Mix1 scintillator is comprised, by weight, of 25% P11 and 75% P43. The "Mix2" scintillator was designed with a different proportion of the same two scintillator components to be somewhat quenching. The Mix2 scintillator is comprised, by weight, of 12.5% P11 and 87.5% P43.

A scaling factor was applied to the P46, Mix1 and Mix2 measurements so the plateau region (starting at 0 cm depth) of all 4 data sets lie on the same curve. As the curves approach the Bragg peak, they separate due to whether they exhibit quenching or not, relative to the ion chamber response. As is evident from FIG. 9, the Mix1 output matches the Markus chamber output very well and the Mix2 output exhibits some quenching, though not as much as the P46 scintillator.

Measurements such as those shown in FIG. 9 indicate how well the detection measurements match a characteristic, in this case defined by the ion chamber response. Although the detection measurements with the Mix2 scintillator do not match the characteristic, the method described above could be used to adjust the detection response, namely, a filter could be added with higher transmission for blue light than yellow-green light. That would have the effect of enhancing the anti-quenching component of the signal.

In addition to dosimetry, other characteristics of the deposited radiation may be of interest. For example, the efficacy of radiation therapy is a function of the relative biological efficiency (RBE) of a particular radiation beam. Different types of radiation—photons or protons or heavier ions—have different RBE values and the RBE may be a function of the LET value. FIG. 7 shows the RBE values as a function of LET for various probabilities of cell survival. So, it may be desirable to measure a detection signal that is appropriately weighted to match the RBE of the radiation beam for a given probability of cell survival. If the scintillator components have a different light output per unit energy depending on LET, then scintillator mixtures can be produced with light outputs that match the appropriate RBE of the beam for a given probability of cell survival.

A properly designed system has the detection signal proportional to the desired characteristic. Especially as treatment modes incorporate very narrow pencil beams, the incident fluence may increase to the point where the luminous efficiency (light output) $E_n$(LET, F) of one or more scintillator components is not linear with the fluence F but saturates with increasing fluence. If there is significant differential non-linearity of the scintillator components, the detection signal may only be linear with the characteristic to the required accuracy for a limited range of fluence. Since pencil radiation beams typically have a Gaussian intensity profile, the fluence varies as a function of position, and the linear measurement may only be achievable over a portion of the beam spot.

The system design can be tuned so the linear range corresponds with the clinically relevant range of fluence. In this fashion, measurement of a characteristic of the beam that is limited to a range of fluence can be linearized with the multiple component scintillator. Furthermore, a changeable optical filter, either by replacement or use of a variable filter, can be used to dynamically tune the optical system. Thus one filter (or setting of a variable filter) can be used for one range of fluence and another filter (or setting of a variable filter) can be used for a different range of fluence.

The discussion above shows how a custom spectral filter can compensate for the detailed characteristics of a particular mixture scintillator. Filter selection can also compensate for other non-idealities of the detector system or enhance certain performance characteristics. For example, components of a scintillator may have different linear ranges as a function of the incident fluence. A spectral filter can be selected to enhance the signal contribution from a scintillator component with a large linear range as a function of the fluence. Changing the filter can also compensate for some aging effects of the detector or the scintillator. For example, if radiation damage to the scintillator or a lens results in relative changes to their spectral transmission, installing a filter with the opposite relative changes can make the detector output insensitive to these aging effects.

In a preferred embodiment of the system, a multi-color image of the scintillator is formed. The multi-color image contains color and intensity information, i.e., two or more spectral component images with significantly non-overlapping spectral content. A detection signal can be produced by an arbitrary linear combination of the spectrally distinct component images. In particular, an output proportional to the desired characteristic can be formed by combining two or more of the spectral component images with the appropriate weighting factors.

The multi-color image of the scintillator can be formed in a variety of ways known to the art. Examples include video cameras with a patterned array of color filters overlaid on a single focal plane sensor, typically a CCD or CMOS array. These cameras record intensity at each pixel, but color information has lower resolution since the intensity of several neighboring pixels with different color filters are compared to derive the local color of the image. An example with comparable color and intensity resolution known to the art is a video cameras with a color separation prism and 3 CCDs to separately record red, green, and blue (RGB) component images.

Figure 11:
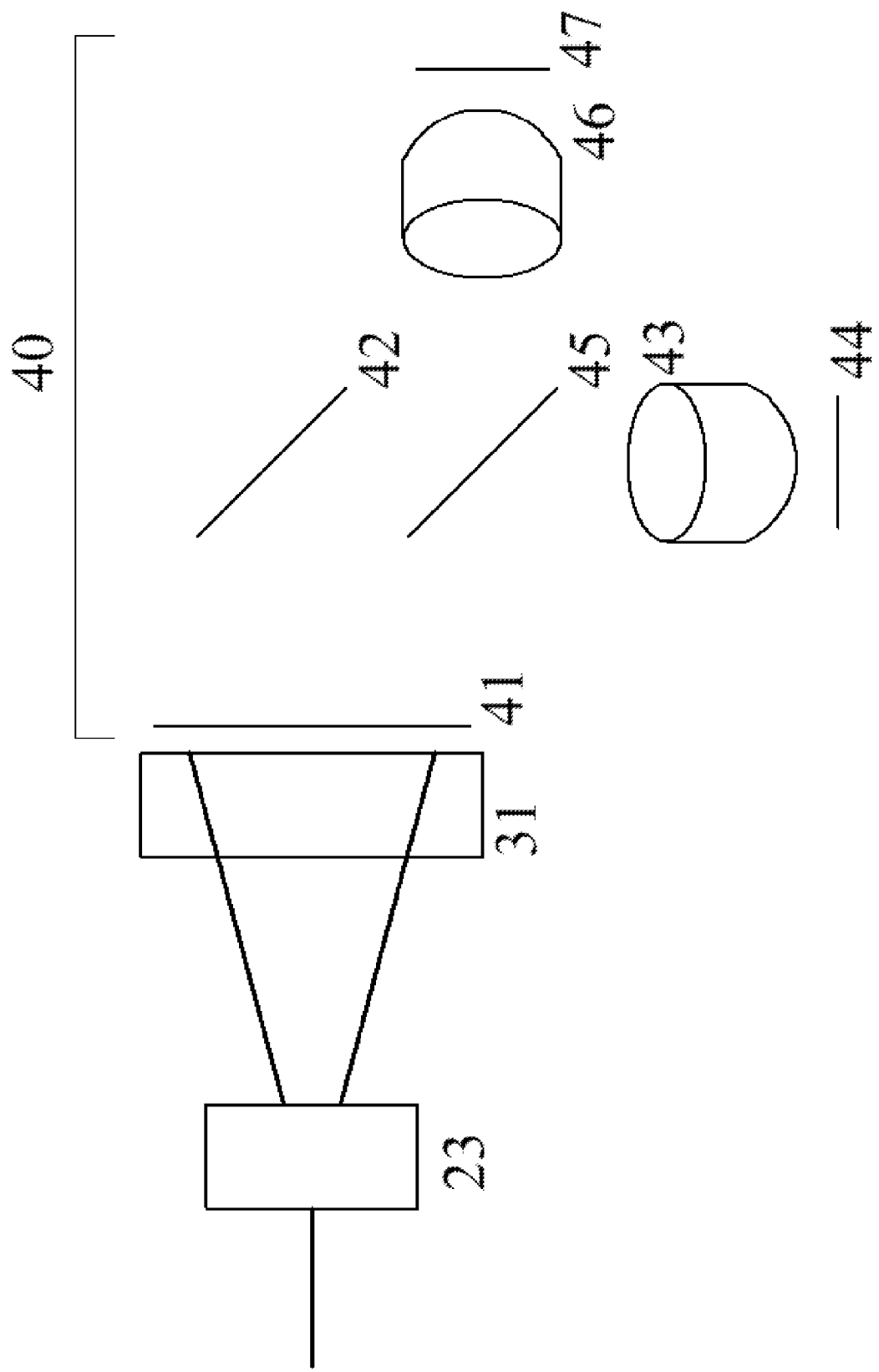
FIG. 11 shows an apparatus which records multiple images of the scintillator.

An optimal detector for a two component scintillator may only record two color components whose spectral content is matched to the scintillator components. In a preferred embodiment, shown in FIG. 11, a dichroic mirror 45 separates the blue output of P11 and the yellow-green output of P43 and dual images are recorded by using two separate imaging sensors 44 and 47. Alternatively, the dual images could be spatially multiplexed onto a single imaging sensor. The two images can be spatially registered and co-added with a weighting factor that produces the best fit to linearize the output with respect to the desired characteristic, e.g., the water-equivalent dose. Before co-adding the images, standard two-point correction (spatially variable bias and gain) or a more complex correction is applied to each spectrally distinct image so it is a linear representation of the incident light in the corresponding spectral band.

More complicated detection signals can be synthesized from the two (or more) spectral images than simply co-adding the images with a single weighting factor. If one or more of the scintillator components exhibits saturation with increasing fluence, a non-linear function of the spectral images can be constructed that linearizes the output with respect to fluence, as well as the desired characteristic. This can be implemented by calibrating the response and modeling the output signal at each pixel as a polynomial function of the corresponding pixel in each spectrally distinct image. Alternatively, a lookup table that is indexed by the corresponding value from each separate image can be used.

MODIFICATIONS

The described embodiments of the invention are intended to be merely exemplary and numerous variations and modifications will be apparent to those skilled in the art. All such variations and modifications are intended to be within the scope of the present invention as defined in the appended claims.

What is claimed is:

1. An apparatus for determining the spatial distribution and intensity of a penetrating radiation beam characterized generally by a propagation direction inside a body, the apparatus comprising:
   a tissue phantom disposed between a radiation source and a radiation detector;
   a scintillating screen disposed behind the tissue phantom for emitting light in response to the radiation received by the scintillating screen, the scintillating screen comprising a mixture of at least two scintillators wherein each scintillator has a different characteristic response and a different spectral output;
   a means of optical communication between the output of the scintillating screen and at least one imaging sensor, wherein the means of optical communication has a nonuniform spectral transmission; and
   at least one imaging sensor in optical communication with the scintillating screen for providing a high resolution imaging sensor output indicative of the spatial distribution and intensity of the radiation beam, wherein the imaging sensor has a nonuniform spectral sensitivity;
   wherein the composition of the scintillating screen, the means of optical communication, and the at least one imaging sensor form a system wherein the relative contribution of the at least two scintillators of the mixture produce an imaging sensor output which is proportional to a characteristic of the radiation beam incident on the scintillating screen at each measurement position accessible with the tissue phantom;
   wherein each scintillator of the mixture contributes a detection signal per deposited energy $D_n(LET,F) = \int d\lambda \rho_n S_n(\lambda) E_n(LET,F) A_n(\lambda) Q(\lambda) T(\lambda)$ to the total imaging sensor output and a fractional contribution $$f_n = \frac{D_n(LET, F)}{\sum_i D_i(LET, F)}$$

to the total imaging sensor output;
   wherein n is the index of the nth scintillator in the mixture, $D_n(LET,F)$ is the detection signal per deposited energy for the nth scintillator as a function of the linear energy transfer (LET) and fluence (F), $\rho_n$ is the areal density of the nth scintillator, $S_n(\lambda)$ is the characteristic spectrum of the nth scintillator, $E_n(LET,F)$ is the luminous efficiency of the nth scintillator as a function of the linear energy transfer (LET) and fluence (F), $A_n(\lambda)$ is the attenuation factor for the nth scintillator due to self-absorption and scattering by the scintillation layer, $Q(\lambda)$ is the spectral sensitivity of the imaging sensor, and $T(\lambda)$ is the spectral transmission of the means of optical communication;
   and wherein the fractional contribution, $f_n$, of at least one scintillator of the mixture to the sensor output varies by at least 3% from what it would be with a means of optical communication having uniform spectral transmission $T(\lambda)=1$ and with the at least one imaging sensor having uniform spectral sensitivity $Q(\lambda)=1$ for a beam with LET and fluence that is clinically relevant.

2. The apparatus as set forth in claim 1, wherein the characteristic of the radiation beam is the dose.

3. The apparatus as set forth in claim 1, wherein the characteristic of the radiation beam is the response of an ion chamber.

4. The apparatus as set forth in claim 1, wherein the characteristic of the radiation beam is the relative biological efficiency.

5. The apparatus as set forth in claim 1, wherein the scintillating screen comprises a mixture of at least two inorganic scintillators.

6. The apparatus as set forth in claim 1, wherein the at least two scintillators are chosen from the group consisting of P11, P20, P43, P46, and P47.

7. The apparatus as set forth in claim 1, wherein the at least two scintillators comprise P11 and P43.

8. The apparatus as set forth in claim 1, wherein the scintillating screen comprises a planar screen disposed perpendicular to the propagation direction of the radiation beam.

9. The apparatus as set forth in claim 1, wherein the means of optical communication comprise a fold mirror and a compound lens.

10. The apparatus as set forth in claim 1, wherein the at least one imaging sensor comprises a CCD.

11. The apparatus as set forth in claim 1, wherein the tissue phantom comprises polymer sheets.

12. The apparatus as set forth in claim 1 wherein the tissue phantom comprises water.

13. The apparatus as set forth in claim 1 wherein the means of optical communication include at least one filter with nonuniform spectral transmission.

14. The apparatus as set forth in claim 1 wherein the means of optical communication include at least one filter with variable nonuniform spectral transmission.

15. The apparatus as set forth in claim 1 wherein the at least one imaging sensor forms a multi-color image.

16. The apparatus as set forth in claim 1 wherein the means of optical communication includes a dichroic mirror which separates the light emitted by the scintillating screen into two significantly non-overlapping spectral bands and forms two spatially distinct images on the at least one imaging sensor, and further wherein the two spatially distinct images are linearly combined to produce the high resolution imaging sensor output.

17. The apparatus as set forth in claim 1 wherein the characteristic of the radiation beam includes the fluence.

18. The apparatus as set forth in claim 7 wherein P11 has areal density $\rho_1$, P43 has areal density $\rho_2$, and the total areal density, $\rho_1+\rho_2$, is in the range 40-400 mg/cm$^2$, and wherein the fractional density of P11, $$\frac{\rho_1}{\rho_1 + \rho_2},$$

is in the range 10-40% and the fractional density of P43, $$\frac{\rho_2}{\rho_1 + \rho_2},$$

is in the range 60-90%.

19. The apparatus as set forth in claim 13 wherein the fractional contribution, $f_n$, of at least one scintillator of the mixture varies by at least 3% from what it would be with a filter having uniform spectral transmission.

\* \* \* \* \*